United States Patent [19]

Pettersen et al.

[11] Patent Number: 5,534,531

[45] Date of Patent: Jul. 9, 1996

[54] COMPOUNDS

[75] Inventors: Erik O. Pettersen, Oslo; Rold O. Larsen, Langesund; John M. Dornish, Bekkestua; Bernt Børretzen, Heistad; Reidar Oftebro, Hvalstad; Thomas Ramdahl, Eiksmarka, all of Norway

[73] Assignee: Norsk Hydro A.S., Oslo, Norway

[21] Appl. No.: 5,979

[22] Filed: Jan. 19, 1993

[30] Foreign Application Priority Data

Jan. 21, 1992 [GB] United Kingdom .................. 9201274

[51] Int. Cl.⁶ .................. A61K 31/425; A61K 31/335
[52] U.S. Cl. .................. 514/365; 514/374; 514/438; 514/452; 514/649; 514/699; 549/13; 549/315; 548/146; 548/215; 558/418; 558/423
[58] Field of Search .................. 549/315, 13; 514/452, 514/438, 374, 649, 699; 548/215, 146; 558/418, 423, 365

[56] References Cited

U.S. PATENT DOCUMENTS 4,874,780 10/1989 Borretzen et al. .................. 514/452
5,149,820 9/1992 Borretzen et al. .................. 548/215

*Primary Examiner*—C. Warren Ivy
*Assistant Examiner*—Amelia Owens
*Attorney, Agent, or Firm*—Wenderoth, Lind & Ponack

[57] ABSTRACT

New compounds having the general formula I

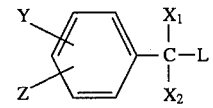

wherein L may be H or D; Y may be CN or

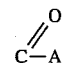

wherein A may be H, D, alkyl with 1–4 carbon atoms, OR wherein R is H or alkyl with 1–4 carbon atoms, or $CR_1R_2R_3$ wherein $R_1$, $R_2$ and $R_3$ are the same or different and are H or alkyl with 1–4 carbon atoms; Z is H, D, Y or alkyl with 1–4 C-atoms, halogen, nitro, amino, monoalkyl amino or dialkyl amino wherein the alkyl groups have 1–4 C atoms, or OR wherein R may be H or alkyl with 1–4 C-atoms, or $CR_4R_5R_6$ wherein $R_4$, $R_5$ and $R_6$ may be the same or different and may be H or F; $X_1$ and $X_2$ may be the same or different and may be OR, $NR_1R_2$ or SR, wherein R, $R_1$ and $R_2$ may be the same or different and may be alkyl having 1–22 carbon atoms which may be branched or straight chained and/or may be further substituted; or $X_1$ and $X_2$ may together with the carbon atom to which they are bound form a cyclic acetal, thioacetal, dithiane, aminal, oxazolidine or thiazolidine; and pharmaceutically acceptable salts thereof.

The compounds are useful as anti-cancer agents and as agents useful for the treatment of illnesses arising due to an abnormally elevated cell-proliferation.

4 Claims, No Drawings

COMPOUNDS

The present invention concerns new compounds which may be useful as agents in the treatment of patients afflicted with cancer, especially carcinoma, or illnesses which arise due to an elevated cell proliferation. The compounds according to the present invention are acetal derivatives of benzaldehydes, which carry a carboxyl group, derivative or analogue on the phenylgroup of the benzylidene moiety.

TECHNICAL FIELD

It is known among other from EP215395, J63264411, J88009490, J55069510 and EP283139 that benzaldehydes and derivatives thereof have an anti-cancer effect. These compounds exert an inhibitory action on the protein synthesis of the cells.

In solid tumours this reduced protein synthesis may result in a lack of vital proteins which lead to cell death. In normal cells there is a potential capacity for protein synthesis which is higher than in most cancer cells of solid tumours. This is demostrated by comparison of the cell cycle duration in normal stem cells, which is often below 10h, and that of most cancer cells of solid tumours, which is typically 30–150h (see Gavosto and Pileri in: *The Cell Cycle and Cancer.* Ed. :Baserga, Marcel Dekker Inc., N.Y. 1971, pp 99). Since cells, as an average, double their protein during a cells cycle, this means that protein accumulation is higher in growth-stimulated normal cells than in most types of cancer cells.

Keeping in mind this difference between normal and cancer cells, there is another difference of similar importance: while normal cells respond to growth-regulatory stimuli, cancer cells have a reduced or no such response. Thus, while normal cells, under ordinary growth conditions, may have a reserve growth potential, cancer cells have little or no such reserve. If a mild protein synthesis inhibition is imposed continuously over a long period of time on normal cells as well as on cancer cells it is probable that the two different types of cells will respond differently: Normal tissue may take into use some of its reserve growth potential and thereby maintain normal cell production. Cancer tissue however, has little or no such reserve. At the same time the rate of protein accumulation in most cancer cells is rather low (i.e. protein synthesis is only a little greater than protein degradation). Therefore the mild protein synthesis inhibition may be just enough to render the tumour tissue imbalanced with respect to protein accumulation, giving as a result a negative balance for certain proteins. During continuous treatment for several days this will result in cell inactivation and necrosis in the tumour tissue while normal tissue is unharmed.

It is known from UK Patent application 9026080.3 that benzaldehyde compounds, previously known as anti-cancer agents may be used for combatting diseases resulting from an abnormally elevated cell proliferation. Such compounds also exert an effect on cells having an abnormally elevated cellular proliferation rate, and thus according to present invention the compounds of formula I may be used for the treatment of diseases such as psoriasis, inflammatory diseases, rheumatic diseases and allergic dermatologic reactions.

Dermatologic abnormalities such as psoriasis are often characterized by rapid turnover of the epidermis. While normal skin produces ca. 1250 new cells/day/cm² of skin consisting of about 27,000 cells, psoriatic skin produces 35,000 new cells/day/cm² from 52,000 cells. The cells involved in these diseases are however "normal" cells reproducing rapidly and repeatedly by cell division. While the cell cycle of normal skin cells is approximately 311 hours, this progression through the division cycle is reduced to about 10 to 36 hours for psoriatic skin.

It is known that benzaldehydes and certain acetal derivatives therof have a growth-inhibitory effect on human cells which is by its nature reversible. Growth inhibition induced by these compounds is primarily due to a reduction in the protein synthesis by cells. (Pettersen et al., Eur. J.Clin. Oncolo. 19, 935–940 (1983) and Cancer Res. 45, 2085–2091 (1985)). The inhibition of protein synthesis is only effective as long as these agents are present in the cellular microenvironment. The synthesis of cellular protein is, for instance, rapidly restored to its normal level within one hour from the time when the agent is removed from the cells.

This leads to the surprising effect that the normal cells are left without damage after treatment with the compounds according to formula I. Furthermore, the inhibition of protein synthesis achieved induces a prolonged cell cycle duration such that a reduction of the cell production as well as a reduction of protein synthesis is achieved during treatment. Therefore diseases for which the symptomatic cause is an enhanced cell proliferation rate can be treated with the compounds of formula I without this leading to cell death—a condition unwanted since the cells involved are normal cells with an abnormal cell proliferation rate.

Examples of diseases which may be treated by the compounds of formula I are rheumatoid arthritis, psoriatic arthritis, systemic lupus erythematosus (SLE), discoid lupus erythematosus (DLE), acne, Bechterew's arthritis, systemic scleroderma and seborrhea.

In EP283139 it was reported that the substitution of the aldehyde hydrogen with a deuterium in the benzylidene moiety leads to an even stronger inhibition of the protein synthesis. Further, it was reported that those new compounds had a longer half life in the cells.

It has now surprisingly been found that the introduction of a carboxylic group, derivative or analogue as substituent on the phenyl group in such compounds gives a stronger inhibition of the protein synthesis.

DETAILED DESCRIPTION

The compounds of the present invention have the general formula (I):

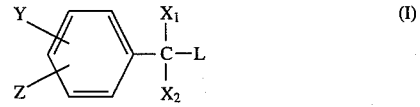

wherein L may be H or D; Y may be CN or

wherein A may be H, D, alkyl with 1–4 carbon atoms, OR wherein R is H or alkyl with 1–4 carbon atoms, or $CR_1R_2R_3$ wherein $R_1$, $R_2$ and $R_3$ are the same or different and are H or alkyl with 1–4 carbon atoms;

Z is H, D, Y or alkyl with 1–4 C-atoms, halogen, nitro, amino, monoalkyl amino or dialkyl amino wherein the alkyl groups have 1–4 C atoms, or OR wherein R may be H or alkyl with 1–4 C-atoms, or $CR_4R_5R_6$ wherein $R_4$, $R_5$ and $R_6$ may be the same or different and may be H or F;

$X_1$ and $X_2$ may be the same or different and may be OR, $NR_1R_2$ or SR, wherein R, $R_1$ and $R_2$ may be the same or different and may be alkyl with 1–22 carbon atoms, which may be branched or straight chained and/or may be further substituted or $X_1$ and $X_2$ may together with the carbon atom to which they are bound form a cyclic acetal (O,O), thioacetal (O,S), diathiane (S,S), aminal (N,N), oxazolidine (O,N) or thiazolidine (S,N); and pharmaceutically acceptable salts thereof.

The phenyl ring of the compounds of formula I may carry one or several groups Z, at the most four Z groups. It is most preferred when there are several Z groups present that these groups are the same or that at least one of them is a further carboxylic group or derivative or analogue.

As shown by formula I above the group Y being a carboxylic group, derivative or analogue substituent on the phenyl ring includes groups such as carboxylic acids, esters, keto groups, acid halogenids, aldehydes, amides and cyano groups. In the remainder of the text, these groups for convenience will be simply denoted "carboxylic groups".

When Z is deuterium this means that the phenyl ring may be partly or fully deuterated, carrying at the most four deuterium atoms on the phenyl ring.

When any group is alkyl it is most preferred methyl or ethyl.

The halogens may be any of chlorine, bromine, iodine or fluorine.

The carboxylic group, Y, may be in the positions 2, 3 or 4 for compounds of formula I wherein Z is H, but the most preferred position is number 4. These compounds may be represented by the following general formula (II):

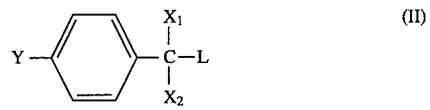

In compounds of formula I, wherein Z is not H, the carboxylic group Y, may be in any of the 2, 3, 4, 5 or 6 positions.

When Z is carboxylic group and there are more than one substituent Z, one of which is an additional carboxylic group, most preferred positions for the two carboxylic groups will be in the 2 and 6 positions or the 3 and 5 positions depending on the position and influence of the other substituent Z and the group Y.

PREPARATION

The acyclic derivatives according to this invention may be prepared according to well-known procedures by reacting the corresponding aldehyde with an alcohol, thioalcohol or secondary amine having alkyl groups with 1–22 carbon atoms.

The cyclic derivatives of the present invention may be prepared by well-known processes for preparing acetals from aldehydes such as reacting the substituted benzaldehyde or lower acetals thereof with a di- or polyhydric alcohol in the presence of an acidic catalyst.

These reactions may conveniently be carried out in a dipolar solvent such as dimethyl formamide, dimethyl sulphoxide, dimethyl acetamide or the like.

Similarly, the preparation of the oxazolidines, aminals, thioacetals, dithianes and thiazolidines proceeds in a conventional manner by reacting the substituted benzaldehyde with the corresponding aminoalcohols, diamines, thioalcohols, dithiols and thioamines respectively.

These reactions are carried out in solvents which form an azeotropic mixture with the water formed in the reaction. Typical solvents used are inert hydrocarbons, preferably benzene or toluene, which are capable by azeotropically removing the water formed, to drive the reaction to a completion.

The reaction conditions and solvents used will in each individual reaction depend on the reactivity and solubility of the reactants.

Generally the compounds according to the present invention may be prepared as shown below in the reaction scheme for the preparation of substituted benzylidene ascorbic acid acetals:

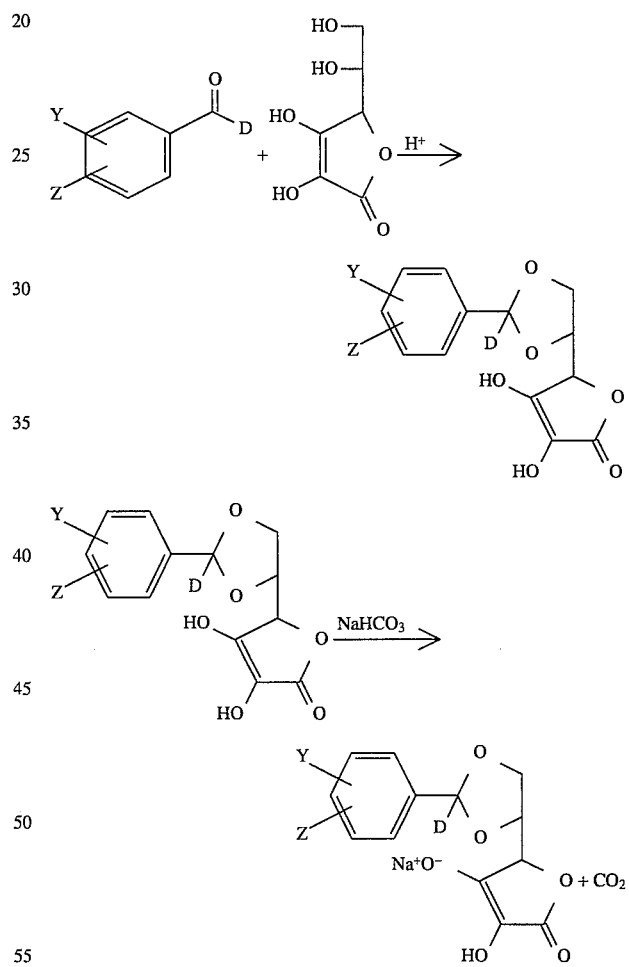

The compounds of formula I wherein L is deuterium may be prepared as described above, but starting with deuterated benzaldehydes derivatives, which may carry one or more further substituents on the phenyl ring, or lower acetales thereof.

The following examples are illustrative of how the compounds of the present invention may be prepared.

EXAMPLE 1

PREPARATION OF SODIUM-5,6-(4-CARBOMETHOXY)-BENZYLIDENE-L-ASCORBATE-$d_1$

STEP 1

PREPARATION OF 4-CARBOMETHOXYBENZOYLCHLORIDE

Monomethyl terephthalate (10.2 g, 0.057 mol) and thionylchloride (50 ml) were mixed in a 100 ml three-necked flask and stirred under gentle reflux overnight. The cooling water was shut off and excess thionylchloride swept away in a stream of nitrogen. By raising the temperature, the product then was distilled and collected as white crystals of high purity.

Yield: 7.2 g, 64% of theoretical.

STEP 2

PREPARATION OF METHYL-4-FORMYLBENZOATE-$d_1$

4-Carbomethoxy benzoylchloride (7.2 g, 0.036 mol), quinolinesulphur * (37 μl stock solution), 5% Pd on $BaSo_4$ (370 mg) and a mixture of deuterated aromatic solvents (100 ml) were refluxed under mechanical stirring in a 250 ml three-necked flask. Deuterium gas was bubbled through, and the reaction followed by GC. Simultaneously, the exhaust gas was bubbled into water (100 ml) in a separate flask and analysed by titrating with 1N NaOH.

After 29 hours, the reaction was nearly completed. The catalyst was then filtered off and the filtrate vigourously stirred for 3 days with a $Na_2S_2O_5$-solution in heavy water (20 g). The aldehyde-sulphite complex thus formed was isolated by filtering and decomposed by stirring for 4 hours with 5% $Na_2CO_3$ solution in heavy water (100 ml). The milky suspenison was extracted with ether (3×300 ml) and the combined extracts dried ($MgSo_4$), filtered and evaporated to give the pure aldehyde as a white solid, mp. 62°–63.5° C. Yield: 3.95 g, 66% of theoretical. The degree of deuteration was 96.3%, as analysed by NMR.

*A stock solution was made by refluxing sulphur (1 g) in freshly distilled quinoline (6 g) for 5 hours and diluting to 70 ml in a mixture of deuterated aromatic solvents.

STEP 3

PREPARATION OF SODIUM-5,6-(4-CARBOMETHOXY)-BENZYLIDENE-L-ASCORBATE-$d_1$

Methyl-4-formylbenzoate-$d_1$ (6.0 g, 0.036 mol) and L-ascorbic acid (6.4 g, 0.036 mol) were dissolved in dry dimethylformamide (50 ml) in a 250 ml flask. Conc. sulphuric acid (0.5 ml) was carefully added, and the reaction mixture left on the rotary evaporator connected to a water jet vacuum source for 3 days. The solvent was then driven off by evaportaing overnight using an oil pump. To the viscous water (75 ml) was added dropwise, raising the pH to 6. The solution was freeze-dried and the crude product rinsed on a prepacked reversed phase column (Lobar C), eluting with 5% methanol/water. Product fractions from 6 runs were freeze-dried and combined to give the title compound as a fluffy solid, 6.2 g, 50% of the theoretical yield. The degree of deuteration was shown by NMR to be 98.1%.

EXAMPLE 2

PREPARATION OF SODIUM 5,6-(3-DEUTEROFORMYL)-BENZYLIDENE-L-ASCORBATE-$d_1$

STEP 1

PREPARATION OF ISOPHTHALDEHYDE-(BIS-1,3-PROPANE-DITHIOACETAL)

Isophthaldehyde (10 g, 0.075 mole), 1,3-propanedithiol (15 ml, 0.15 mole), paratoluene sulphonic acid (spatual tip) and toluene (150 ml) were mixed and boiled under reflux for 20 hours. A small amount of hexane and a few drops of diisopropyl ester were added, and the solution cooled. The crystals which precipitated were filtered and dried.

The preparation gave 17 g of the title compound, 74% of theoretical yield.

STEP 2

PREPARATION OF ISOPHTHALDEHYDE-(BIS-1,3-PROPANE-DITHIOACETAL)-$d_2$

Isophthaldehyde-(bis-1,3-propanedithioacetal) (10 g, 32 mmole) was dissolved in dry tetrahydrofuran (THF) (200 ml) in a 500 ml three-necked round-bottomed flask equipped with septum. The apparatus was dry and under argon. The solution was cooled to −60° C. Butyl lithium (60 ml 1.6M BuLI, 96 mmole) was added slowly via the septum, while the temperature was held at −50° C. After three hours a precipitate had formed (the lithium salt of dithiane). After a reaction time of 4 hours the temperature had reached −30°. $D_2O$ (30 ml) was added and stirred until the temperature had reached +5° C. The reaction mixture was filtered, leaving wet crystals. The raw product was dissolved in dichloromethane, washed with 2M hydrochloric acid and water, dried with magnesium sulphate and evaporated to dryness leaving 6 g of product. This was recrystalised from ethylacetate giving 4 g of brilliant white crystals.

The mother liquor was worked-up by evaporation and recrystallisation giving 2.9 g product.

The preparation gave a total yield of 6.9 g, 68% of theoretical.

STEP 3

SYNTHESIS OF DEUTERATED ISOPHTHALALDEHYDE (Ref. A. V. Rama Rao et al., Tetrahedron, 43,779(1987))

Isophthalaldehyde-bis-dithioacetal-$d_2$, (1.8 g, 0.057 moles), $HgCl_2$, (6.8 g, 0.025 moles), and HgO (2.7 g, 0.013 moles) were dissolved in a 9:1 mixture of acetonitril and water. The reaction mixture was boiled at reflux for 1.5 h. After the reaction mixture has been cooled to room temperature, the insoluble mercury salts are filtered off. The filtrate is then washed twice with a 5% ammonium acetate solution. After removing the formed crystals, the product is taken up in dichloromethane. The organic phase is then evaporated to dryeness, giving yellow crystals. The product is finally recrystallised from dichloromethane, giving 0,5 g of slightly yellow crystals, mp. 86°–87° C.

The GC-MS of the product shows one peak with the molecular ion in the mass spectrum at m/e 136, which confirms the structure of isophthalaldehyde-$d_2$, $C_8H_4D_2O_2$, Mw.136.

STEP 4

PREPARATION OF SODIUM 5,6-(3-DEUTERO-FORMYL)-BENZYLIDENE-L-ASCORBATE-$d_1$

To a solution of isophthalaldehyde-$d_2$ (6.0 g, 0.044 mol) and L-ascorbic acid (7.7 g, 0.044 mol) in N,N-dimethylformamide (65 ml) was carefully added conc. $D_2SO_4$ (1 ml) and the mixture stirred at room temperature under $N_2$ for 2 days. The reaction mixture was evaporated in the vacuum from a waterjet for 2 days, then from an oil pump overnight, giving a viscous residue. The pH was raised to about 6 by the careful addition of 10% $NaHCO_3$, and the solution evaporated overnight. The residue was dissolved in 7.5% methanol/water (50 ml), filtered on a 0.45 μm Millipore filter and evaporated to give a 76% pure yellow solid (12.2 g). This crude product was purified by preparative chromatography on a prepacked reversed phase column (Lobar C) eluting with 7.5% methanol/water.

By freeze-drying and combining the product fractions, a total of 2.1 g pure substance was collected (15% of theoretical). The degree of deuteration was indicated by NMR to be better than 96%.

EXAMPLE 3

PREPARATION OF SODIUM-5,6-(4-CARBOMETHOXY)-BENZYLIDENE-L-ASCORBATE.

4-formyl benzoic acid methylester (30 g, 0.18 mol), ascorbic acid (32 g, 0.18 mole) and dimethyl formamide (DMF) (145 g) were mixed in a 250 ml three-necked round-bottomed flask. Concentrated sulphuric acid was carefully added and the mixture allowed to stand at room temperature for approx. 20 hours. The DMF was then removed by rotary evaporation.

The raw product was neutralised with sodium hydrogen carbonate solution (15.3 g in 150 ml $H_2O$), and evaporated to dryness. The resulting product was further purified by preparative HPLC (Waters RP-8 column).

The preparation gave 10.4 g product, the identity of which was confirmed by $^1$H-NMR spectroscopy at 300 MHz.

EXAMPLE 4

PREPARATION OF SODIUM-5,6-(3-FORMYL)-BENZYLIDENE-L-ASCORBATE

Isophthalaldehyde (25 g, 0.186 mol), ascorbic acid (33 g, 0.187 mol) and dry dimethyl formamide (DMF) (130 ml) were mixed in a 250 ml 3-necked round-bottomed flask. The reaction was initiated by the slow addition of conc. $H_2SO_4$ (2.5 ml). The mixture was stirred for approx. 20 hours under inert atmosphere ($N_2$).

The DMF was removed by evaporation under vacuum for 20 hours at 50° C. This gave 76 g of the raw product, a yellow syrup. The product was neutralized by the addition of sodium hydrogen carbonate ($NaHCO_3$) (18 g) dissolved in water, which caused effervescence (pH 6). When the evolution of gas had ceased the water was evaporated off. This gave a yellow voluminous powder.

The salt was further purified using Walters preparative HPLC, RP-18 column and the required fraction evaporated.

The final yield obtained was 22 g product, 40% of theoretical.

The identity, structure and purity of the product were confirmed by $^1$H-NMR spectroscopy at 300 MHz.

EXAMPLE 5

PREPARATION OF SODIUM-5,6-(3-CYANO)-BENZYLIDENE-L-ASCORBATE

In a 100 ml glass reactor 3,5 g (0.027 moles) of 3-cyanobenzaldehyde and 4.7 g (0.027 moles) of L-ascorbic acid were dissolved in 25 ml dry dimethylformamide (DMF). The reaction was started by slowly adding 0.4 ml conc. sulphuric acid. The reaction was performed with stirring under an inert atmosphere ($N_2$) at room temperature for 2 days.

The reaction mixture was then evaporated under high vacuum at a temperature of maximum 40° C. During the evaporation the reaction goes further to completion as shown by GLC analysis of the trimethylsilyl ether. After most of the DMF had been removed, (>90%), the raw product was neutralized with 2.2 g sodium bicarbonate in 30 ml water. After the $CO_2$ evolution had ceased, the solution was evaporated under high vacuum (<2 mBar) at max. 40° C.

The product was further purified by preparative HPLC on a RP-8 column to remove unreacted starting materials. The yield of the final product, sodium 5,6-(3-cyano)-benzylidene-L-ascorbate, was 3 g ( 35%).

The structure was confirmed by $^1$H-NMR spectroscopy at 300.13 MHz.

EXAMPLE 6

PREPARATION OF SODIUM-5,6-(4-FORMYL)-BENZYLIDENE-L-ASCORBATE

In a 100 ml glass reactor, 7.5 g (0.)56 moles) terephtalaldehyde and 9.8 g (0.056 moles) L-ascorbic acid were dissolved in 50 ml dry dimethylformamide (DMF). The reaction was started by adding slowly 1 ml conc. sulfuric acid. The reaction was performed with stirring under an inert atmosphere ($N_2$) over night at room temperature.

The reaction was then evaporated under high vacuum at a temperature of maximum 40° C. During the evaporation the reaction goes to completion as shown by GLC analysis of the trimethylsilyl ethers. After most of the DMF has been removed, (>90%), the raw product is neutralized with 7.3 g sodium carbonate in 80 ml water. After the $CO_2$ evolution has ceased, the solution is evaporated under high vacuum (2<mBar) at max. 40° C.

The product was further purified by preparative HPLC on a RP-18 column. The yield of the final product sodium 5,6-(4-formyl)-benzylidene-L-ascorbate is 8.4 g (40%). The structure was confirmed by $^1$H-NMR spectroscopy at 300.13 MHz.

Biological Experiments

In the following in vitro experiments, the rate of protein synthesis was measured for a compound from the prior art, which is deuterated sodium 5,6-O-benzylidene-L-ascorbate (zilascorb($^2$H)) and for five compounds according to the present invention.

Cell Culturing Techniques and Synchronization

Human cells of the established line NHIK 3025, originating from a cervical carcinoma in situ (Nordbye, K. and Oftebro, R., Exp. Cell Res., 58: 458, 1969), Oftebro, R. and Nordbye, K., Exp. Cell Res., 58: 459–460, 1969) were cultivated in medium E2a (Puck et al., J. Exp. Med., 106: 145–165, 1957) supplemented with 20% human (prepared at the laboratory) and 10% horse serum (Grand Island Biological Co.).

The cells are routinely grown as monolayers in tissue culture flasks. The cells were kept in continuous exponential growth by frequent reculturing, i.e. every second and third day, and were obtained by repeated selection of mitotic cells (Pettersen et al., Cell Tissue Kinet., 10: 511–522, 1977). During reculturing as well as during experiments the cells were kept in a walk-in incubator at 37° C. Under growth conditions as used here, the NHIK 3025 cells have a medium cell-cycle time of ~18 hr, with medium $G_1$, $S_1$ and $G_2$ durations of ~7, ~8 and ~2.5 hr, respectively.

Protein Synthesis:

The rate of protein synthesis was calculated as described previously (Rønning et al., J. Cell Physiol., 107: 47–57, 1981). Briefly, cellular protein was labeled to saturation during a 2-day preincubation with [$^{14}$C]valine of constant specific radioactivity (0.5 Ci/mol) prior to the experiment. This was achieved by using a high concentration of valine so that the dilution of [$^{14}$C]valine by intracellular valine and by proteolytically generated valine will be negligible (Rønning et al., Exp. Cell Res., 123: 63–72, 1979), thus keeping the specific radioactivity at a constant level. The rate of protein synthesis was calculated from the incorporation of [$^3$H] valine of constant specific activity. The incorporated measurements were related to the total of [$^{14}$C] radioactivity in protein at the beginning of the respective measurement periods and expressed as the percentage per hr (Rønning et al., J. Cell. Physiol., 107: 47–57, 1981).

Results

The protein synthesis inhibition induced by Zilascorb($^2$H) and the five compounds of the present invention was measured in human NHIK 3025 cells after administration of the compounds at a concentration of 0.3 mM or 0.5 mM. In table 1 the rate of protein synthesis is given in per cent relative to an untreated control. The values presented represent one experiment, and are a mean of 3 samples ± standard error.

TABLE 1

| SUBSTANCE | FORMULA | CONC. [mM] | RATE OF PROTEIN SYNTHESIS [%] |
|---|---|---|---|
| SODIUM-5,6-(3-DEUTEROFORMYL)-BENZYLIDENE-L-ASCORBATE-$d_1$ | | 0.3 | 73.3 ± 12.8 |
| SODIUM-5,6-(3-FORMYL)-BENZYLIDENE-L-ASCORBATE | | 0.3 | 93.6 ± 4.2 |
| SODIUM-5,6-(3-CYANO)-BENZYLIDENE-L-ASCORBATE | | 0.3 | 73.3 ± 6.8 |
| SODIUM-5,6-(4-CARBOMETHOXY)-BENZYLIDENE-L-ASCORBATE | | 0.3 | 81.4 ± 3.6 |

TABLE 1-continued

| SUBSTANCE | FORMULA | CONC. [mM] | RATE OF PROTEIN SYNTHESIS [%] |
|---|---|---|---|
| SODIUM-5,6-(4-CARBOMETHOXY)-BENZYLIDENE-L-ASCORBATE-$d_1$ | 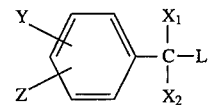 | 0.5 | 69.7 ± 1.0 |
| ZILASCORB ($^2$H) |  | 0.3 | 89.2 ± 1.5 |

Several other experiments have shown the same type of effect.

According to present invention the compounds of formula I may be administrered to a patient in need of anti-cancer treatment or to a patient suffering from diseases which arise due to an abnormally elevated cell proliferation.

For this purpose the compounds may be formulated in any suitable manner for administration to a patient either alone or in admixture with suitable pharmaceutical carriers or adjuvants.

It is especially preferred to prepare the formulations for systemic therapy either as oral preparations or parenteral formulations.

Suitable enteral preparations will be tablets, capsules, e.g. soft or hard gelatine capsules, granules, grains or powders, syrups, suspensions, solutions or suppositories. Such will be prepared as known in the art by mixing one or more of the compounds of formula I with non-toxic, inert, solid or liquid carriers.

Suitable parental preparations of the compounds of formula I are injection or infusion solution.

When administered topically the compounds of formula I may be formulated as a lotion, salve, cream, gel, tincture, spray or the like containing the compounds of formula I in admixture with non-toxic, inert, solid or liquid carriers which are usual in topical preparations. It is especially suitable to use a formulation which protects the active ingredient against air, water and the like.

The preparations can contain inert or pharmacodynamically active additives. Tablets or granulates e.g. can contain a series of binding agents, filler materials, carrier substances and/or diluents. Liquid preparations may be present, for example, in the form of a sterile solution. Capsules can contain a filler material or thickening agent in addition to the active ingredient. Furthermore, flavour-improving additives as well as the substances usually used as preserving, stabilizing, moisture-retaining and emulsifying agents, salts for varying the osmotic pressure, buffers and other additives may also be present.

The dosages in which the preparations are administrered can vary according to the indication, the mode of use and the route of administration, as well as to the requirements of the patient. In general a daily dosage for a systemic therapy for an adult average patient in need of anti-cancer treatment will be about 0.1–500 mg/kg body weight/day, preferably 2–200 mg/kg body weight/day.

The daily dosage for a systemic therapy for an adult average patient in need of treatment for elevated cell-proliferation will be about 0.1–50 mg/kg/day preferably 1–15 mg/kg/day. For topic administration, the suitable salve or ointment can contain from 0.1–50% by weight of the pharmacetical formulation, especially 1–20%.

If desired the pharmaceutical preparation of the compound of formula I can contain an antioxidant, e.g. tocopherol, N-methyl-tocopheramine, butylated hydroxyanisole, ascorbic acid or butylated hydroxytoluene.

We claim:

1. A compound of the formula I $$\underset{Z}{\overset{Y}{\diagdown}}\!\!\!\diagdown\!\!\!\diagdown\!\!\!\underset{X_2}{\overset{X_1}{\underset{|}{\overset{|}{C}}-L}}$$

wherein L may be H or D;

Y may be CN or $$\underset{C-A}{\overset{O}{\diagup\!\!\!\!/}}$$

wherein A may be H, D, alkyl with 1–4 carbon atoms, OR wherein R is H or alkyl with 1–4 carbon atoms, or $CR_1R_2R_3$ wherein $R_1$, $R_2$ and $R_3$ are the same or different and are H or alkyl with 1–4 carbon atoms;

Z is H, D, Y or alkyl with 1–4 C-atoms, halogen, nitro, amino, monoalkyl amino or dialkyl amino wherein the alkyl groups have 1–4 C atoms, or OR wherein R may be H or alkyl with 1–4 C-atoms, or $CR_4R_5R_6$ wherein $R_4$, $R_5$ and $R_6$ may be the same or different and may be H or F;

$X_1$ and $X_2$ may be the same or different and may be OR, $NR_1R_2$ or SR, wherein R, $R_1$ and $R_2$ may be the same or different and may be alkyl having 1–22 carbon atoms which may be branched or straight chained and/or may be further substituted; or $X_1$ and $X_2$ may together with the carbon atom to which they are bound form a cyclic acetal, thioacetal, dithiane, aminal, oxazolidine or thiazolidine;

or a pharmaceutically acceptable salt thereof.

2. A compound according to claim 1, wherein L is D.

3. A compound according to claim 1, wherein L is H.

4. A pharmaceutical composition comprising a compound of the formula

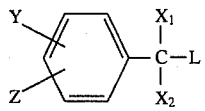

wherein L may be H or D;

Y may be CN or

wherein A may be H, D, alkyl with 1–4 carbon atoms, OR wherein R is H or alkyl with 1–4 carbon atoms, or $CR_1R_2R_3$ wherein $R_1$, $R_2$ and $R_3$ are the same or different and are H or alkyl with 1–4 carbon atoms;

Z is H, D, Y or alkyl with 1–4 C-atoms, halogen, nitro, amino, monoalkyl amino or dialkyl amino wherein the alkyl groups have 1–4 C atoms, or OR wherein R may be H or alkyl with 1–4 C-atoms, or $CR_4R_5R_6$ wherein $R_4$, $R_5$ and $R_6$ may be the same or different and may be H or F;

$X_1$ and $X_2$ may be the same or different and may be OR, $NR_1R_2$ or SR, wherein R, $R_1$ and $R_2$ may be the same or different and may be alkyl having 1–22 carbon atoms which may be branched or straight chained and/or may be further substituted; or $X_1$ and $X_2$ may together with the carbon atom to which they are bound form a cyclic acetal, thioacetal, dithiane, aminal, oxazolidine or thiazolidine;

or a pharmaceutically acceptable salt thereof, and a pharmaceutically acceptable carrier, diluent and/or excipient.

* * * * *

UNITED STATES PATENT AND TRADEMARK OFFICE
CERTIFICATE OF CORRECTION

PATENT NO. : 5,534,531
DATED : July 9, 1996
INVENTOR(S) : ERIK OLAI PETTERSEN, ROLF OLAF LARSEN, JOHN MICHAEL DORNISH, BERNT BØRRETZEN, REIDAR OFTEBRO and THOMAS RAMDAHL It is certified that error appears in the above-indentified patent and that said Letters Patent is hereby corrected as shown below:

On the Title page of the patent in Section [75] Inventors, correct the name of the second listed inventor to read "Rolf O. Larsen".

On the Title page of the patent in Section [75] Inventors, correct the name of the fourth listed inventor to read "Bernt Børretzen".

Signed and Sealed this

Eighteenth Day of February, 1997

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,534,531
DATED : July 9, 1996
INVENTOR(S) : Pettersen, et al

It is certified that error appears in the above-identified patent and that said Letters Patent is hereby corrected as shown below:

On the title page, item [75], Inventor: "Rold O. Larsen" should read
-- Rolf O. Larsen --

Signed and Sealed this

Eighteenth Day of March, 1997

*Attest:*

BRUCE LEHMAN

*Attesting Officer*  *Commissioner of Patents and Trademarks*